(12) United States Patent
Festal et al.

(10) Patent No.: US 6,339,097 B1
(45) Date of Patent: Jan. 15, 2002

(54) N-PHENYLAMIDE AND N-PYRIDYLAMIDE DERIVATIVES, METHOD OF PREPARING THEM AND PHARMACEUTICAL COMPOSITIONS CONTAINING THEM

(75) Inventors: Diedier Festal, Ecully; Jean Yves Nioche, Limonest; Guy Augert, Chanoz; Jacques Deserprit, Miribel, all of (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/581,991
(22) PCT Filed: Dec. 11, 1998
(86) PCT No.: PCT/EP98/08101
§ 371 Date: Jun. 21, 2000
§ 102(e) Date: Jun. 21, 2000
(87) PCT Pub. No.: WO99/33825
PCT Pub. Date: Jul. 8, 1999

(30) Foreign Application Priority Data

Dec. 23, 1997 (FR) .............................. 97 16399

(51) Int. Cl.$^7$ ................ A61K 31/4433; A61K 31/4436; C07D 405/12; C07D 409/12
(52) U.S. Cl. .................... 514/338; 514/342; 546/279.7; 546/281.1; 546/282.7
(58) Field of Search ............................ 546/279.7, 281.1, 546/282.7; 514/338, 342

(56) References Cited

U.S. PATENT DOCUMENTS 5,491,152 A   2/1996  Wilde et al. ................ 514/336

FOREIGN PATENT DOCUMENTS

| EP | 298466 | | 1/1989 |
| EP | 380392 | | 8/1990 |
| EP | 420266 | | 4/1991 |
| EP | 420266 A2 | * | 4/1991 |
| EP | 481383 | | 4/1992 |
| EP | 0481383 | * | 4/1992 |
| EP | 585913 | * | 3/1994 |

OTHER PUBLICATIONS

C. Djerassi et al. : Journal of Organic Chemistry, vol. 565, No. 18, 1991, pp. 5360–5368.

* cited by examiner

*Primary Examiner*—Alan L. Rotman
*Assistant Examiner*—Rita Desai
(74) *Attorney, Agent, or Firm*—Millen, White, Zelano & Branigan, P.C.

(57) ABSTRACT

The present invention relates to the compounds of formula (I) in which X, $R_1$, $R_{2\ and\ R3}$ are as defined in claim 1. These compounds are cholesteryl acyl transferase (ACAT) inhibitors.

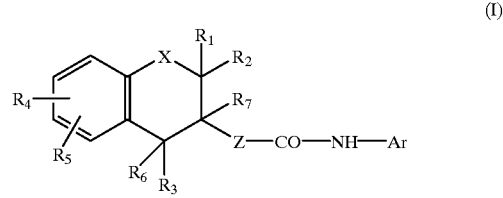

(I)

17 Claims, No Drawings

N-PHENYLAMIDE AND N-PYRIDYLAMIDE DERIVATIVES, METHOD OF PREPARING THEM AND PHARMACEUTICAL COMPOSITIONS CONTAINING THEM

The present invention relates to new N-phenyl-amide and N-pyridylamide derivatives, to the methods of preparing these compounds, to the pharmaceutical compositions containing them and to their use as medicaments especially in the treatment of hyperlipidaemia and atherosclerosis.

It is known that lipid deposits, especially cholesterol deposits in blood vessels are responsible for the formation of atheroma plaques which are the cause of a variety of cardiovascular diseases; more precisely, atheroma is a form of atherosclerosis characterized by an excessive accumulation of lipids, in particular of cholesterol esters, in the wall of the vessels; it has recently been found that an enzyme, acyl Coenzyme A: Cholesteryl Acyl transferase (ACAT) is responsible for the esterification of cholesterol, and a correlation was found between the increase in the activity of this enzyme and the accumulation of cholesterol esters in the vascular wall; it is also known that dietary cholesterol is absorbed in free form and is then esterified by intestinal ACAT for release into the bloodstream in the form of VLDL (very low density lipids) and/or of chylomicrons.

While several ACAT inhibitors have been identified (see for example: EP 295 637, EP 415 413 or EP 497 201) the development of new ACAT inhibitors having improved therapeutic properties should be continued.

Attempts have been made to develop ACAT-inhibiting products capable of preventing intestinal absorption of dietary and bile cholesterol and of acting against the deposition of cholesterol esters in the wall of the vessels.

This search for ACAT inhibitors has led the inventors to develop a new family of N-phenylamide and N-pyridylamide derivatives and to find that these products manifest a potent vascular ACAT-inhibiting activity associated with an intense antihyperlipidaemic effect on various animal species.

These properties of the compounds of the invention make them particularly useful especially for the treatment of hyperlipidaemia and of athero-sclerosis.

The compounds of the invention have, more precisely, the formula:

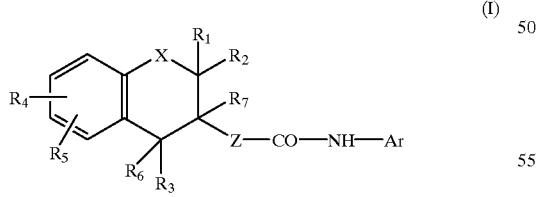

in which X is O, S or $CH_2$;

$R_1$ and $R_2$, which may be identical or different, are hydrogen, $(C_1-C_6)$alkyl or $(C_3-C_8)$cycloalkyl, or alternatively $R_1$ and $R_2$, together with the carbon atom bearing them, form $(C_3-C_8)$cycloalkyl;

$R_3$ is a $(C_6-C_{12})$aryl optionally substituted with one or more Y radicals, which may be identical or different; or a 5- to 7-membered heteroaryl comprising 1 to 3 endocyclic heteroatoms chosen from O, S and N which is optionally substituted with one or more Y radicals, which may be identical or different;

Y is halogen, a $(C_1-C_6)$alkyl optionally substituted with one or more halogens, a $(C_1-C_6)$alkoxy optionally substituted with one or more halogens, a $(C_1-C_6)$alkylthio optionally substituted with one or more halogens, $(C_1-C_7)$acylamino, $(C_1-C_3)$acyloxy, hydroxyl, nitro, cyano, amino, $(C_1-C_6)$alkylamino, di-$(C_1-C_6)$-alkylamino, pyrrolidono, piperidino, morpholino, $(C_1-C_4)$ alkylsulfonylamino, $(C_2-C_5)$ alkoxycarbonyl, carboxyl, $(C_2-C_6)$alkylcarbonyl, carbamoyl, $(C_2-C_5)$alkylcarbamoyl, di-$(C_2-C_5)$ aalkylcarbamoyl or $(C_1-C_6)$alkylsulfonyl;

$R_4$ and $R_5$, which may be identical or different, are a Y radical or alternatively a hydrogen atom;

Ar is one of the following groups A, B or C:

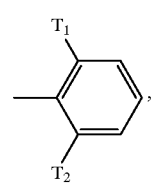

A

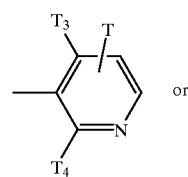

B

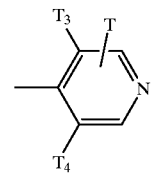

C $T_1$ and $T_2$, which may be identical or different, are halogen, $(C_1-C_6)$alkoxy, $(C_1-C_6)$alkylthio or $(C_1-C_6)$ alkyl;

T is a hydrogen atom or $(C_1-C_6)$ alkyl;

$T_3$ and $T_4$, which may be identical or different, are $(C_1-C_6)$ alkyl, $(C_1-C_6)$ alkoxy, $(C_1-C_6)$ alkylthio, $(C_6-C_{12})$arylthio, $(C_1-C_6)$alkoxycarbonyl, $(C_1-C_6)$ alkyl-carbonyl, $(C_6-C_{12})$arylcarbonyl or —$(CH_2)_p$—OR in which p is 1, 2, 3 or 4 and R is $(C_2-C_3)$ alkyl, $R_6$ and $R_7$ are each a hydrogen atom or alternatively $R_6$ and $R_7$ together are a bond;

z is either (i) the divalent group —$CHR_9$— in which $R_9$ is a hydrogen atom or $(C_1-C_6)$alkyl;

or (ii) the divalent group —$CHR_{10}$—$CHR_{11}$— in which $R_{10}$ and $R_{11}$ together form a bond such that Z is —CH=CH—or alternatively $R_{10}$ and $R_{11}$, which may be identical or different, are as defined above for $R_9$;

or (iii) the divalent group —$CHR_{12}$—$CHR_{13}$—$CH_2$— in which $R_{12}$ and $R_{13}$ together form a bond such that Z is —CH=CH—$CH_2$—, or alternatively $R_{12}$ and $R_{13}$, which may be identical or different, are as defined above for $R_9$, as well as their addition salts with a pharmaceutically acceptable acid or base.

The addition salts of these compounds with pharmaceutically acceptable acids or bases also form part of the invention. Examples of these salts are the salts formed from hydrochloric acid, p-toluenesulfonic acid, fumaric acid, citric acid, succinic acid, salicylic acid, oxalic acid, hydrobromic acid, phosphoric acid, methanesulfonic acid, tartaric acid and mandelic acid.

In some cases, the compounds of the invention have one or more chiral centres. It should be understood that each stereoisomer forms part of the invention.

$(C_1-C_6)$Alkyl is a linear or branched, saturated hydrocarbon radical of 1 to 6 carbon atoms. The $(C_1-C_6)$alkoxy group consequently is the alkyl-O— group and the $(C_1-C_6)$ alkylthio group is the alkyl-S— group where alkyl is as defined above.

Moreover, $(C_3-C_8)$cycloalkyl is understood to mean a saturated mono- or bicyclic hydrocarbon radical comprising from 3 to 8 carbon atoms. Examples are cyclopropyl, cyclohexyl, cyclopentyl and cycloheptyl.

The term $(C_6-C_{12})$aryl is, moreover, a mono- or polycyclic aromatic group having 6 to 12 carbon atoms, such as phenyl, naphthyl or anthryl. Thus, $(C_6-C_{12})$arylthio is the $(C_6-C_{12})$-aryl-S— radical.

As a 5- to 7-membered heterocycle comprising 1 to 3 endocyclic heteroatoms chosen from O, S and N, there may be mentioned furan, thiophene, pyrrole, oxazole, thiazole, imidazole, pyrazole, isoxazole, isothiazole, pyridine, pyridazine, pyrimidine and pyrazine.

The halogen atoms are chlorine, bromine, fluorine and iodine.

The term acyl is the alkylcarbonyl radical. Thus, $(C_1-C_7)$ acylamino is $(C_1-C_7)$alkylcarbonylamino and $(C_1-C_3)$ acyloxy is $(C_1-C_3)$alkylcarbonyloxy.

Among these compounds, there are 6 subgroups of preferred compounds.

A first subgroup consists of compounds of formula I in which Y is halogen, $(C_1-C_6)$alkyl, $(C_1-C_6)$alkoxy or trifluoromethyl.

A second subgroup comprises the compounds of formula I in which:

$R_1$ and $R_2$, which may be identical or different, are hydrogen or alternatively $R_1$ and $R_2$, together with the carbon atom bearing them, form $(C_3-C_8)$cycloalkyl;

$R_3$ is a $(C_6-C_{12})$aryl optionally substituted with one or more Y radicals, which may be identical or different;

Y is halogen;

$R_4$ and $R_5$ are each a hydrogen atom;

Ar is one of the following groups A, B or C:

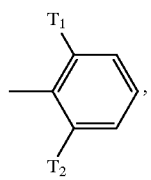

A

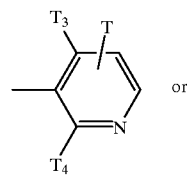

B or

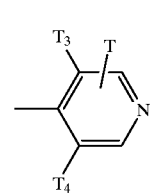

C $T_1$ and $T_2$, which may be identical or different, are $(C_1-C_6)$ alkyl;

T is a hydrogen atom or $(C_1-C_6)$alkyl;

$T_3$ and $T_4$, which may be identical or different, are $(C_1-C_6)$alkyl; $(C_1-C_6)$alkoxy or $(C_1-C_6)$alkylthio;

$R_6$ and $R_7$ are each a hydrogen atom or alternatively $R_6$ and $R_7$ together are a bond;

Z is either
  (i) the divalent group —$CHR_9$— in which $R_9$ is a hydrogen atom or $(C_1-C_6)$alkyl; or
  (ii) the divalent group —$CHR_{10}$—$CHR_{11}$— in which $R_{10}$ and $R_{11}$ together form a bond such that Z is —CH=CH—, or alternatively $R_{10}$ and $R_{11}$ are each a hydrogen atom.

A third subgroup consists of the compounds of formula I in which Z is —$CHR_{12}$—$CHR_{13}$—$CH_2$—, $R_{12}$ and $R_{13}$ being as defined above.

Among the compounds of the first, second and third subgroups defined above, those for which $R_1$ and $R_2$ are a hydrogen atom are more particularly preferred.

A fourth subgroup consists of the compounds of formula I in which X is O or S and $R_1$ and $R_2$, together with the carbon atom bearing them, form a $(C_3-C_8)$ cycloalkyl.

A fifth subgroup of preferred compounds comprises the compounds of formula I in which X is O or S and Z is —CH=CH— or alternatively —CH=CH—$CH_2$.

In general, it is preferable that Ar is 2,4-dimethylthio-6-methyl-3-pyridyl; 2-methoxy-4-hexylthio-3-pyridyl and 2,6-diisopropylphenyl.

A sixth subgroup consists of the compounds of formula I in which X is $CH_2$.

Among these compounds, those for which Ar is a group B or C are more particularly preferred. Here again, the meanings 2,4-dimethylthio-6-methyl-3-pyridyl and 2-methoxy-4-hexylthio-3-pyridyl for Ar are particularly advantageous.

According to a preferred embodiment of the invention, $R_3$ is preferably phenyl which is optionally substituted, pyridyl or thienyl which is optionally substituted, such as for example 2-pyridyl or 2-thienyl which is optionally substituted at the 5-position.

The compounds of the invention may be prepared by coupling an acid of formula II

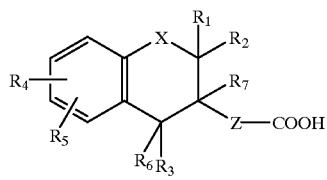

(II)

in which $R_1$, $R_2$, $R_3$, $R_4$, $R_5$, $R_6$, $R_7$ and Z are as defined in claim 1, with an aromatic amine of formula III:

Ar—NH$_2$ (III)

in which Ar is as defined above.

This method, as well as the preferred variants of this method which are described below, are a subject of the invention.

The coupling of the acid of formula II with the amine of formula III may be simply carried out by reacting the amine of formula III with an activated derivative of the acid of formula II such as an acid chloride, an ester or a mixed anhydride.

More precisely, persons skilled in the art know that they can envisage the amination of the following activated acid derivatives: $P_o$—CO—SH, $P_o$—CO—SR, $P_o$—CO—Se—Me, $P_o$—CO—B(OR)$_2$, $(P_o$—COO)$_4$Si, $P_o$—CO—C (hal)$_3$ or $P_o$—CO—N$_3$ in which $P_o$ is:

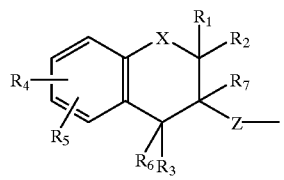

hal is a halogen atom, and

R is (C$_1$-C$_6$)alkyl.

The methods of activating organic acids are known in the art.

Moreover, the coupling of the acid of formula II with the amine III may be carried out using any of the techniques used in liquid-phase peptide synthesis.

These techniques are, for example, described in "Methods of Peptide Synthesis" T. Wieland and H.

Determann, Angew. Chem. Interm. Ed. Engl., 2, 358, (1963).

By way of example, the chlorides of the acid of formula II may be obtained by the action of SOCl$_2$, oxalyl chloride, PCl$_3$ or PCl$_5$.

It is also possible to prepare an acid chloride by the action of triphenylphosphine, in carbon tetrachloride, on the acid of formula II.

For the preparation of an acid bromide, the corresponding brominated reagents, such as oxalyl bromide, PBr$_3$ or PBr$_5$, may be used.

As an example of preparation of a mixed anhydride, there may be mentioned the action of bis(2-oxo-3-oxazolidinyl) phosphinic acid on the acid of formula II. This reaction is preferably carried out in the presence of a base as in the majority of activating reactions. This base may be either pyridine, ethylenediamine or 4-dimethylaminopyridine.

Thus, according to a preferred embodiment of the invention, the compounds of formula I are prepared:

using the following steps (i) and (ii):
(i) an acid of formula II is treated with oxalyl chloride in the presence of dimethylformamide; and then
(ii) an amine of formula III is reacted with the compound obtained in step (i);
or alternatively
using the following steps (i) and (ii):
(i) an acid of formula II is treated with bis(2-oxo-3-oxazolidinyl)phosphinic acid in the presence of a base; and then
(ii) an amine of formula III is reacted with the compound obtained in step (i).

The following two operating protocols can for example be used for coupling the acid II with the amine III.

Method A:

According to this method, the acid of formula II is activated in the form of an acid chloride before being coupled to the amine III.

The reaction of oxalyl chloride with the acid of formula II is carried out in an apolar aprotic solvent such as a hydrocarbon, for example a halogenated hydrocarbon.

The oxalyl chloride and a catalytic quantity of dimethylformamide are added to a solution of the compound of formula II, kept at a temperature of between 15 and 25° C. and preferably at room temperature. The reaction medium is then heated to a temperature of between 30 and 70° C., for example the reflux temperature of the solvent used. The reaction is monitored by thin-layer chromatography. The solvent is then evaporated and the residue is taken up in an apolar aprotic solvent such as, for example, the halogenated hydrocarbon previously used, before being supplemented with the aromatic amine III and with a base such as pyridine or 4-dimethylaminopyridine. This reaction is continued for the length of time necessary at a temperature of between 15 and 85° C., preferably at room temperature.

Method B:

According to this method, the acid of formula II is activated in the form of a mixed anhydride before being coupled to the amine III.

A weak base such as triethylamine is added to a solution of the acid of formula II in an apolar aprotic solvent such as a halogenated hydrocarbon, and then the reaction medium is heated to a temperature of between −10 and 10° C., preferably between 0 and 5° C. Bis(2-oxo-3-oxazolidinyl) phosphinic acid chloride is then added. When the reaction is complete, the aromatic amine of formula III is added to the reaction medium all at once, the latter being kept between −10 and 10° C. (preferably between 0 and 5° C.). A base in solution in an apolar aprotic solvent such as a halogenated hydrocarbon is then introduced in small portions to the reaction medium.

The compound of formula I obtained is then isolated and purified.

The amines of formula III are either directly available commercially, or are easily available from commercial products.

In the remainder of the text, methods of preparing the compounds of formula II are provided.

The compounds of formula II in which Z is —CHR$_9$— may be obtained by following the reaction scheme A.

SCHEME A

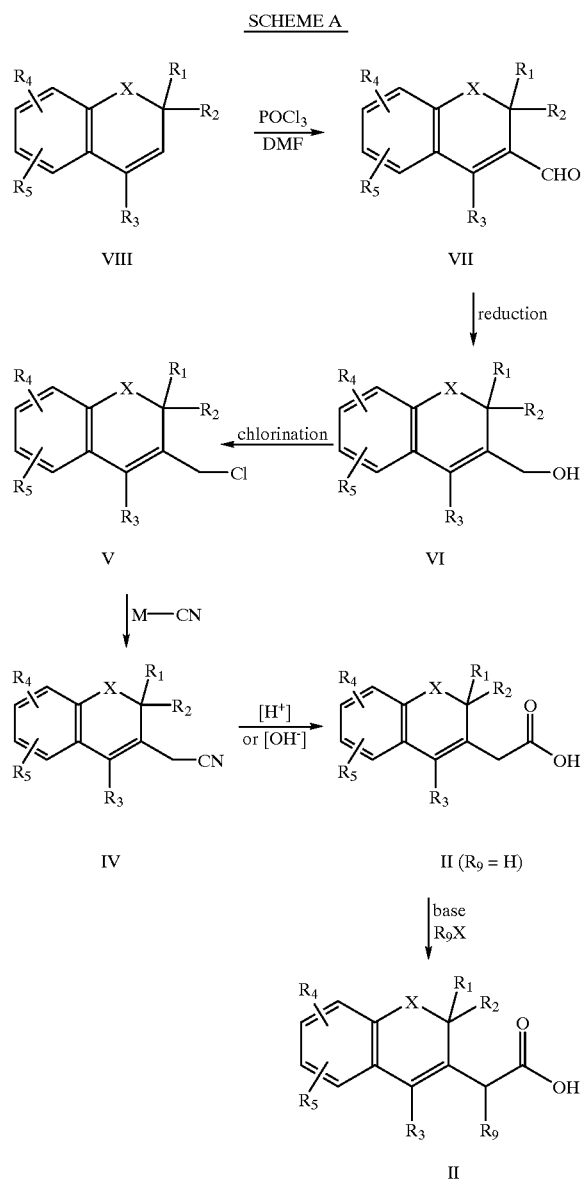

The first step allows the introduction of the carboxaldehyde functional group.

A compound of formula VIII in which R$_1$, R$_2$, R$_3$, R$_4$ and R$_5$ and X are as defined above is reacted with phosphorus oxychloride. This reaction takes place in a preferably polar aprotic solvent such as dimethylformamide (DMF). The reaction temperature varies between −20° C. and room temperature. Preferably, the reaction is carried out between 0° C. and 5° C. and its progress is monitored by thin-layer chromatography. The aldehyde VII obtained is isolated in the usual manner by dilution of the reaction medium in a water-ice mixture, neutralization and then extraction and purification.

The next step of reduction of the aldehyde functional group to a hydroxymethyl functional group is carried out using any of the methods known in the art, as long the reaction conditions are such that they do not cause undesirable side reactions. Where appropriate, the reactive functional groups of the groups R$_1$, R$_2$, R$_3$, R$_4$ and R$_5$ are protected.

Among the reagents commonly used to this end, there may be mentioned lithium aluminum hydride, sodium borohydride or sodium cyanoborohydride. When sodium borohydride is used, the reaction is preferably carried out in a methanol-water mixture at a temperature of between −40 and 0° C., better still between −25 and −15° C. Here again, the compound obtained is isolated in a manner known per se.

The alcohol of formula VI thus isolated is then converted to the corresponding alkyl chloride. This conversion may be carried out in any manner, as long as the reaction conditions are such that they do not cause side reactions. Where appropriate, the reactive functional groups of the groups R$_1$, R$_2$, R$_3$, R$_4$ and R$_5$ are protected.

A known method consists in treating the alcohol VI with thionyl chloride in an inert solvent such as, for example, a toluene- or benzene-type aromatic hydrocarbon, at a temperature of between 15 and 30° C., preferably at room temperature.

Other reagents may be used for the chlorination of the compound VI such as, for example, PCl$_5$, PCl$_3$ or POCl$_3$.

The chlorinated compound of formula V is then treated with an alkali metal cyanide (MCN) such as sodium cyanide in a polar aprotic solvent such as DMF. The reaction temperature is kept between 0 and 50° C. depending on the reactivity of the chloride V. When MCN is sodium cyanide, a temperature of between 20 and 25° C. is generally suitable. The compound of formula IV obtained is isolated and purified in a conventional manner.

The compounds of formula II in which R$_9$ is hydrogen are easily prepared from the nitrile IV by acidic or basic treatment. To this end, the following reagent systems may be used:

NaOH/H$_2$O$_2$ or NaOHaq
H$_2$SO$_4$
HCOOH/HBr or HCl
AcOH/BF$_3$
AcOH/HCl.

For example, the nitrile IV may be hydrolysed using an AcOH/HCl: 40/60 to 60/40 mixture, a 1/1 mixture being perfectly appropriate. In this case, the AcOH/HCl mixture preferably plays the role of solvent, the temperature being unimportant between 0 and 50° C., preferably between 15 and 25° C.

In order to obtain the compounds of formula I in which R$_9$ is (C$_1$–C$_6$)alkyl, the corresponding compound of formula II in which R$_9$ is a hydrogen atom is treated with an alkyl halide of formula R$_9$-X in which X is a halogen atom, a group (C$_1$–C$_6$)alkylsulfonyloxy or (C$_6$–C$_{10}$)arylsulfonyloxy optionally substituted with (C$_1$–C$_6$)alkyl, and R$_9$ is (C$_1$–C$_6$) alkyl, in the presence of a strong base capable of removing the hydrogen at the α position with respect to the carboxyl functional group in the compound of formula II (R$_9$=H). Such a base is, for example, lithium diisopropylamide (LDA).

According to a preferred embodiment, LDA is prepared in situ from n-butyllithium and diisopropylamine at a temperature of between −15 and 5° C., preferably at about 0° C. The solvent used for the generation of LDA is a polar aprotic solvent such as tetrahydrofuran. The halide $R_9$-X and the compound of formula II are then added to the reaction medium. The reaction temperature is, for example, a temperature of between 15 and 35° C., preferably a temperature of between 20 and 25° C.

When the compound of formula I is such that Z is —$CHR_{10}$—$CHR_{11}$—, it may be prepared according to reaction scheme B.

SCHEME B

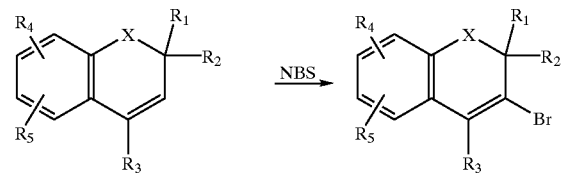

VIII        IX

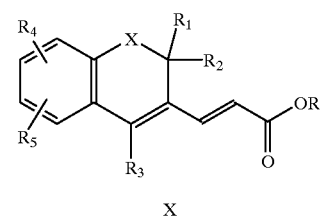

X

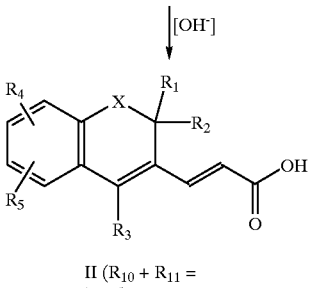

II ($R_{10}$ + $R_{11}$ = bond)

The introduction of a bromine atom into the compound of formula VIII is obtained by the action of N-bromosuccinimide (NBS) on the compound of formula VIII dissolved in a polar aprotic solvent such as dimethylformamide in the absence of moisture. The reaction temperature is for example room temperature. It may nevertheless vary, depending on the reactivity of the compound of formula VIII, between 10 and 35° C.

The next step consists in converting the brominated derivative obtained of formula IX to a compound of formula X. To do this, an alkyl acrylate of formula $H_2C$=CH—COOR in which R=($C_1$–$C_6$)alkyl is reacted with the brominated derivative IX in the presence of palladium acetate, a phosphine and a base. The reaction advantageously takes place in a polar aprotic solvent such as dimethylformamide. The base may be triethylamine, pyridine or 4-dimethylaminopyridine, preferably triethylamine.

The phosphine for example has the formula $PAr'_3$ in which Ar' is preferably a $C_6$–$C_{12}$aryl optionally substituted with a ($C_1$–$C_6$)alkyl. $PAr'_3$ is for example triphenylphosphine or tritolylphosphine.

For the reaction to progress well, the compound of formula IX, dissolved in DMF, the base, the phosphine and the palladium acetate are first brought into contact, then the acrylate of formula $CH_2$=CH—COOR is added to the reaction medium.

The resulting ester of formula X is isolated in a conventional manner and then saponified in a manner known per se to give a compound of formula II in which $R_{10}$ and $R_{11}$ together form a bond.

Starting with this compound, it is possible to easily have access to all the compounds of formula II in which Z is —$CHR_9$—$CHR_{10}$—.

For example, the acid of formula II obtained above:

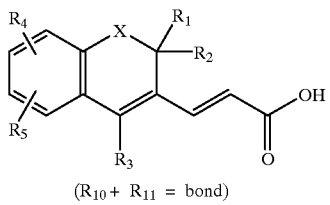

($R_{10}$ + $R_{11}$ = bond)

is subjected to a catalytic hydrogenation. By judiciously controlling the hydrogenation conditions, there is obtained either a compound of formula II in which $R_6$, $R_7$, $R_{10}$ and $R_{11}$ are each a hydrogen atom, or a compound of formula II in which $R_6$ and $R_7$ together form a bond and $R_{10}$ and $R_{11}$ are each a hydrogen atom.

The compounds of formula II in which Z is —$CHR_{12}$—$CHR_{13}$—$CH_2$— may be obtained using a Wittig reaction starting with the aldehyde of formula VII (Scheme A). It is for example possible to use a reagent system composed (i) of a phosphonium halide of formula ROOC—$CH_2$—$CH_2$—$P^+A^3$, hale in which R is hydrogen or ($C_1$–$C_6$)alkyl, hal is halogen and A is chosen from a ($C_6C_{12}$)aryl optionally substituted with ($C_1$–$C_6$)alkyl and (ii) of a base such as an alkali metal tert-butoxide (tBuOK), an alkali metal hydride (NaH) or an alkyl-lithium ($C_4H_9Li$). The reaction may advantageously be carried out in a polar aprotic solvent such as dimethylformamide or tetrahydrofuran at a temperature of between 0 and 30° C.

According to another of its aspects, the invention relates to a pharmaceutical composition comprising at least one compound of formula I, in combination with one or more pharmaceutically acceptable vehicles.

The vehicles which may be used are, for example, fillers, diluents, binders, wetting agents, disintegrating agents, surface-active agents, and lubricants. The pharmaceutical composition may be in any desirable unit form, including tablets, pills, powders, liquids, suspensions, emulsions, granules, capsules, suppositories, injections (solutions and suspensions) and the like.

To prepare tablets, it is possible to use vehicles known in this field, for example excipients, such as lactose, sucrose, sodium chloride, glucose, urea, starch, calcium carbonate, kaolin, crystalline cellulose, silicic acid and the like; binding agents, such as water, ethanol, propanol, a simple syrup, a glucose solution, a starch solution, a gelatin solution, carboxymethylcellulose, gum lac, methyl cellulose, potassium phosphate or polyvinylpyrrolidone and the like; disintegrating agents, such as dried starch, sodium alginate, agar powder, laminaria powder, sodium bicarbonate, calcium carbonate, fatty acid esters of polyoxyethylenesorbitan, sodium lauryl sulfate, a stearic acid monoglyceride, starch, lactose and the like; disintegration inhibitors, such as refined sugar, stearin, cocoa butter, hydrogenated oils and the like; absorption accelerators, such as a quaternary ammonium base, sodium lauryl sulfate and the like, wetting agents, such as glycerin, starch and the like; adsorbing agents, such as starch, lactose, kaolin, bentonite, colloidal silicic acid and the like; a lubricating agent such as purified talc, salts of stearic acid, powdered boric acid, polyethylene glycol and the like.

In the case of the preparation of tablets, the tablets may, moreover, be coated with a customary coating material so as to be converted to sugar-coated tablets, tablets coated with a gelatin film, tablets bearing enteric coatings, film-coated tablets, or tablets with a double layer or with multiple layers.

To form into pills, it is possible to use, for example, known vehicles which are commonly used in this field, such as excipients such as glucose, lactose, starch, cocoa butter, hydrogenated vegetable oils, kaolin or talc and the like; binders, such as powdered gum arabic, powdered gum tragacanth, gelatin, ethanol and the like; and disintegrating agents, such as laminaria powder, agar and the like.

To form suppositories, it is possible to use known vehicles which are widely used in this field, for example polyethylene glycols, cocoa butter, higher alcohols, higher alcohol esters, gelatin, semi-synthetic glycerides and the like.

To produce injectable preparations, solutions and suspensions are sterilized and they are preferably made isotonic with respect to blood. To produce injectable preparations, it is also possible to use vehicles which are commonly used in this field, for example water, ethyl alcohol, propylene glycol, ethoxylated isostearyl alcohol, polyoxylated isostearyl alcohol, fatty acid esters of polyoxyethylenesorbitan and the like. In this case, an appropriate quantity of sodium chloride, glucose or glycerin may be added to the desirable pharmaceutical preparations in order to make the solution isotonic. Furthermore, it is possible to add to the desirable pharmaceutical preparations, where appropriate, dissolving agents, buffer solutions, analgesic agents which are customarily used, as well as colouring agents, preservatives, perfumes, taste-modifying agents, sweetening agents and other medicaments.

The compounds of the invention have proved to be potent inhibitors of acyl-coenzyme A. As such, they are useful in the treatment or the prophylaxis of hypercholesterolaemia, atheromatous atherosclerosis and can even prevent possible ischaemic accidents such as, for example, a myocardial infarction as well as cerebrovascular diseases.

The pharmacological properties of the invention compounds were demonstrated by the following tests.

Test A: measurement of in vitro hepatic ACAT inhibition in rats: male Wistar rats weighing 220–250 g were sacrificed by cervical dislocation; the liver was removed and homogerused to prepare the microsomal fraction by ultracentrifugation; these microsomes were incubated with $^{14}C$-oleyl coenzyme A according to the method described by P. J. GILLIES et al., Exp. and Mol. Pathol. 1986, 44, 329–339; lipids were extracted from the incubate with a methanol-chloroforme mixture and $^{14}C$-oleyl cholesterol was separated by TLC; the latter represented the measurement of the ACAT activity and the results were expressed in inhibitory concentration 50 ($IC_{50}$) representing the concentration of compound inhibiting the ACAT activity by 50%.

As an example, the $IC_{50}$ values of compounds No. 1, 4 and 6 were respectively $94 \times 10^{-9}$ mole/l, $74 \times 10^{-9}$ mole/l and $31 \times 10^{-9}$ mole/l.

Test B: measurement of intestinal absorption of cholesterol in rats; male Wistar rats weighing 230–250 g and fasted for 24 hours received simultaneously the test substance per os and triton WR 1339 by IV route; one hour later, they were again treated orally with $^3H$-cholesterol; three hours later, I ml of blood was taken from the retro-orbital sinus: the blood radioactivity determined on 0.1 ml of serum represented the measurement of the absorption of $^3H$-cholesterol. The results were expressed in effective dose 50 ($ED_{50}$) in mg per kg of animal and represented the quantity of compound inhibiting the intestinal absorption of cholesterol by 50%.

As an example, the $ED_{50}$ values of compounds No. 1, 4 and 6 were respectively 0.005 mg/kg, 0.038 mg/kg and 0.023 mg/kg.

Test C: hypercholesterolemia model; claim 1 compounds were tested by oral route in animals subjected to a cholesterol-rich diet;

As an example, in the male Wistar rat fed a 2.5% cholesterol enriched diet for 8 days and treated for 2 days with compound No. 1, total cholesterol was lowered by 50% at the dose of 0.78 mg/kg; the effect was mainly observed on VLDL (Very Low Density Lipid).

As an example, in the rabbit fed a 0.5% cholesterol enriched diet for 15 days and treated sumultaneously with compound No. 1, total cholesterol was decreased by 70% at the dose of 0.1 mg/kg; the effect was mainly observed on VLDL (Very Low Density Lipid).

The following examples are given by way of illustration as preferred embodiments.

I—Preparation of Aromatic Amines of Formula III

When Ar is 2-($C_1$–$C_6$)alkoxy-4-n-hexylthio-3-pyridyl, the reaction scheme followed is, for example, the following:

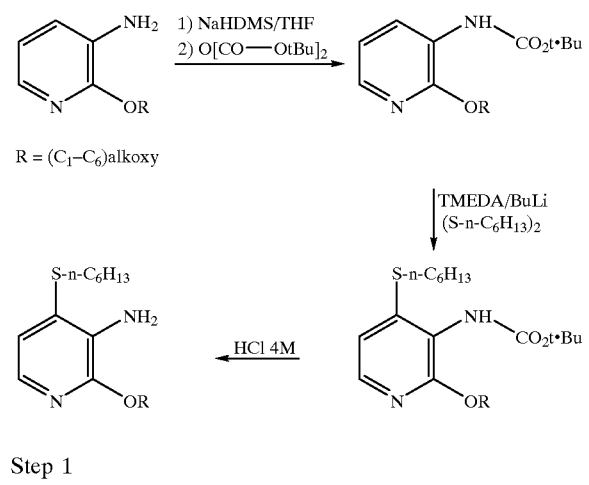

Step 1

Tert-Butyl (2-methoxy-3-pyridyl) carbamate:

3.72 g (30 mmol) of 2-methoxy-3-pyridylamine in solution in 30 ml of tetrahydrofuran are placed in a 100-ml reactor, protected from moisture, and under a nitrogen atmosphere, and then 60 ml (60 mmol) of sodium bis (trimethylsilyl)amide in a 1 M solution in tetrahydrofuran are added dropwise at room temperature.

After stirring the reaction mixture for 20 minutes at room temperature, 6.54 g (30 mmol) of di-tert-butyl carbonate are added dropwise to the reaction medium kept at room temperature.

After stirring at room temperature for 3 hours, the tetrahydrofuran is evaporated off. The residue is taken up in ethyl acetate, washed with water, with hydrochloric acid (0.1 M) and then with water (until a pH of the washings equal to 7 is obtained). After drying the organic phase over sodium sulfate, and evaporation of the solvent, a black oil is obtained which is chromatographed on a silica gel (eluent ethyl acetate-hexane: 1–3). After evaporation of the solvent, 6.1 g of an amber-coloured oil are obtained, that is to say a yield of 90.2%.

TLC: (MERCK "Kieselgel 60" silica gel; AcOEt-hexane: 1–2); Rf=0.4 I.R.: υ NH=3425, CO=1731; NMR: (CDCl$_3$): 1.5 (s, 9H); 3.95 (s, 3H); 6.8 (dd, 1H, J=5 Hz, J=7.8 Hz); 6.9 (s, 1H); 7.7 (dd, 1H, J=5 Hz, J=1.6 Hz); 8.2 (d, 1H, J=7.8 Hz).

Step 2

Tert-Butyl (4-n-hexylthio-2-methoxy-3-pyridyl) carbamate:

4.48 g (20 mmol) of the compound obtained in the preceding step in solution in 100 ml of diethyl ether and 9.05 ml (60 mmol) of tetramethylethylene-diamine are placed in a reactor, protected from moisture, and under a nitrogen atmosphere.

After having cooled the solution to −70° C., 37.5 ml (60 mmol) of n-butyllithium in hexane (1.6 M) are added dropwise. The reaction medium is stirred for 2 hours at −10° C. and then 14.1 g (60 mmol) of dihexyl sulfide are added dropwise at −70° C.

After stirring the solution for 12 hours at room temperature, the reaction medium is taken up in water and extracted with diethyl ether. The organic phase is washed with hydrochloric acid (0.1 M) and then with water until a pH of the washings equal to 7 is obtained, and then finally dried over sodium sulfate. After evaporation of the solvent, an oil is obtained which is chromatographed on a silica gel (eluent ethyl acetate-hexane: 1–5). After evaporation of the solvent, 5.6 g of an oil is obtained which crystallizes, that is to say a yield of 82.3%. Its melting point is between 72 and 74° C.

TLC: (MERCK "Kieselgel 60" silica gel; AcOEt-hexane: 1–3); Rf=0.3 I.R.: υ NH=3171, CO=1720; NMR: (CDCl$_3$): 0.85 (t, 3H); 1.3 (m, 4H); 1.45 (m, 11H); 1.7–1.8 (m, 2H); 3.0 (t, 2H); 4.25 (s, 3H); 6.7 (d, 1H, J=6.8 Hz); 7.85 (d, 1H, J=6.8 Hz).

Step 3

4-n-Hexylthio-2-methoxy-3-aminopyridine 5.6 g (16.45 mmol) of the compound obtained in the preceding step in solution in 140 ml of ethyl acetate and 140 ml of a 4 M hydrochloric acid solution are mixed, with vigorous stirring, in a 500-ml reactor.

The reaction medium is left for 12 hours at room temperature. The reaction medium is then neutralized with sodium bicarbonate (until a pH of the washings equal to 7 is obtained), then the organic phase is washed with water and dried over sodium sulfate and then evaporated off. The oil obtained is chromatographed on a silica gel (eluent: dichloro-methane). After evaporation of the solvent, 3.63 g of an oil are obtained, that is to say a yield of 91.8%.

TLC: (MERCK "Kieselgel 60" silica gel; AcOEt-hexane: 1–3); Rf=0.6; NMR: (CDC$_3$): 0.85 (t, 3H); 1.2–1.3 (m, 4H) 1.3–1.4 (m, 2H); 1.5–1.6 (m, 2H); 2.85 (t, 2H); 3.95 (s, 3H); 4.1 (s, 2H); 6.7 (d, 1H, J=6.7 Hz); 7.4 (d, 1H, J=6.7 Hz).

II—Preparation of the Carboxylic Acids of Formula II in Which Z is —CHR$_{10}$—CHR$_{11}$ 1—3-[Spiro{cyclopentane-1,2'-(4'-(4-fluorophenyl)-2'H-3'-benzopyranyl)}]propanoic acid Step 1

Spiro{cyclopentane-1,2'-(3'-bromo-4'-(4-fluorophenyl)-2'H-benzopyran))

43.4 g (0.3 mol) of N-bromosuccinimide in solution in 500 ml of dimethylformamide are placed in a reactor kept protected from moisture. A solution of 70.1 g (0.25 mol) of spiro{cyclopentane-1,2'-(4'-(4-fluorophenyl)-2'H-benzopyran} in solution in one litre of dimethylformamide is added dropwise to this solution kept at room temperature. The solution is stirred overnight at room temperature and then poured into 3 litres of ice-cold water. The reaction medium is extracted with diethyl ether. The organic solution is then washed with water (until a pH of the washings equal to 7 is obtained), and then dried over sodium sulfate. After evaporation of the solvent, the solid obtained is dispersed in 100 ml of ethanol, placed at −20° C. for 12 hours, and then drained and dried. 68.7 g of the expected product are thus obtained, that is to say a yield of 76.5%. This product has a melting point of between 107 and 109° C. (ethanol).

TLC: (MERCK "Kieselgel 60" silica gel; AcOEt-hexane: 2–100); Rf=0.7.

Step 2

Ethyl 3-{spiro[cyclopentane-1,2'-(4'-(4-fluorophenyl)-2'H-3'-benzopyranyl)]}-prop-2-enoate.

14.1 g (39.25 mmol) of the compound obtained in the preceding step in solution in 40 ml of dimethylformamide are placed in a reactor kept protected from moisture. A solution of 90 ml of triethylamine in solution in 90 ml of dimethylformamide is added dropwise to this solution, kept at room temperature, and then the following reagents are added successively to the reaction medium:

0.72 g (2.3 mmol) of tri(2-tolyl)phosphine;
0.18 g (0.79 mmol) of palladium acetate, and then dropwise at room temperature,
19.55 ml of ethyl acrylate (180.5 mmol).

The reaction medium is then heated under reflux (95° C.) for 2 hours. The reaction medium is then poured over a water/ice mixture and then acidified with a concentrated hydrochloric acid solution of pH equal to 1. The precipitate obtained is extracted with methylene chloride, and then the organic solution is washed with water (until a pH of the washings equal to 7 is obtained), dried over sodium sulfate and evaporated off.

The solid obtained is finally dispersed in 100 ml of ethanol and then drained. 10.5 g of the expected compound are obtained, that is to say a yield of 70.8%. The compound obtained has a melting point of between 138 and 140° C.

TLC: (MERCK "Kieselgel 60" silica gel; AcOEt-hexane: 5–95); Rf=0.3; I.R.: υ C.O=1715 cm$^{-1}$.

Step 3

3-(Spiro[cyclopentane-1,2'-(4'-(4-fluorophenyl)-2'H-3'-benzopyranyl)]}-prop-2-enoic acid.

18.92 g (50 mmol) of the compound obtained in the preceding step are poured into 700 ml of ethanol. 75 ml (75 mmol) of 1 N sodium hydroxide are added to this solution. The reaction medium is then heated under reflux for 40 minutes. After evaporation, the solid obtained is dispersed in diethyl ether and drained. The solid is redissolved in water, the insoluble portion being filtered. The aqueous phase is acidified with hydrochloric acid (to pH=1), and then extracted with ethyl acetate. The organic phase is washed with water (until a pH of the washings equal to 7 is obtained), dried and evaporated off.

The solid obtained is dispersed in pentane and drained.

17.5 g of the expected product are obtained, that is to say a yield of 100%. This product has a melting point of between 172 and 174° C.

TLC: (MERCK "Kieselgel 60" silica gel; AcOEt-hexane: 1–1); Rf=0.46; I.R.: υ C.O=1682 cm$^{-1}$; NMR: (CDCl$_3$): 1.5–2.5 (m, 8H); 5.5–5.8 (d, 1H) 6.5–7.5 (m, 9H); 10 (s, 1H). Percentage analysis: $C_{22}H_{19}FO_3$, 0.25 mol $H_2O$ MW: 354.87.

|  | C | H | N |
|---|---|---|---|
| Calculated % | 74.39 | 5.49 | 5.35 |
| Found % | 74.65 | 5.58 | 5.39 |

Step 4

3-[Spiro{cyclopentane-1,2'-(4'-(4-fluorophenyl)-2'H-3'-benzopyranyl)}]propanoic acid A solution composed of 7 g (20 mmol) of the acid obtained in the preceding step, 170 ml of tetrahydrofuran and 5 g of Raney nickel are heated, with stirring, for 2 hours 30 minutes in an autoclave at a hydrogen pressure of 100 bar, at 60° C. After filtration of the catalyst and evaporation of the solvent, the solid residue is dispersed in hexane and drained. This compound has a melting point of 177° C.

TLC: (MERCK "Kieselgel 60" silica gel; AcOEt-hexane: 1–1); Rf=0.60; I.R.: υ C.O=1706 cm$^{-1}$;

2—Other acids of formula II in which Z is —$CHR_{10}$—$CHR_{11}$—, and their corresponding precursor esters By following the operating protocol described above (II.1) in the case of 3-[spiro{cyclopentane-1,2'-(4'-(4-fluorophenyl)-2'H-3'-benzopyranyl)}]propanoic acid, the following acids of formula II were obtained.

TABLE 1

| Preparation No. | X | $R_{10}$ | $R_{11}$ | $R_3$ | R | $R_1$ | $R_2$ | Melting point (° C.) |
|---|---|---|---|---|---|---|---|---|
| I.2.1 | O | H | H | 4-F—$C_6H_4$ | H | —$(CH_2)_4$— | | 177 |
| I.2.2 | S | H | H | $C_6H_5$ | H | H | H | oil |
| I.2.3 | O | bond | | 4-F—$C_6H_4$ | $C_2H_5$ | —$(CH_2)_4$— | | 138–140 |
| I.2.4 | O | bond | | 4-F—$C_6H_4$ | H | —$(CH_2)_4$— | | 172–174 |
| I.2.5 | S | bond | | $C_6H_5$ | $C_2H_5$ | H | H | oil |
| I.2.6 | S | bond | | $C_6H_5$ | H | H | H | oil |
| I.2.7 | O | bond | | $C_6H_5$ | $C_2H_5$ | H | H | oil |
| I.2.8 | O | bond | | $C_6H_5$ | H | H | H | 216–218 |

In Table 1 above, the term "bond" means that $R_{10}+R_{11}$ together form a bond and 4-F-$C_6H_4$ is the radical of formula

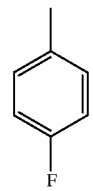

Table 2 assembles the intermediate bromides which led to the compounds of Table 1 above.

TABLE 2

IX ($R_4$ = $R_5$ = H)

| Intermediate No. | X | $R_1$ | $R_2$ | $R_3$ | Melting point (° C.) |
|---|---|---|---|---|---|
| IX. 1 | O | —$(CH_2)_4$— | | 4-F—$C_6H_4$— | 107–109 |
| IX. 2 | S | H | H | $C_6H_5$— | oil |
| IX. 3 | O | H | H | $C_6H_5$— | oil |

III—Preparation of the Carboxylic Acids of Formula II in Which Z is —$CHR_9$—

1—2-(4-Phenyl-2H-3-benzo[b]pyranyl)acetic acid

Step 1

4-Phenyl-2H-3-benzo[b]pyranylcarboxaldehyde.

3.13 litres (40.7 mol) of dimethylformamide are placed in a $^6$-litre reactor, kept protected from moisture and under a nitrogen atmosphere. 748 ml (8.14 mol) of phosphorus oxychloride are added dropwise to this solution, kept between 0 and 5° C. The reaction medium is stirred at 5° C. for 20 minutes, and then 175.28 g (0.814 mol) of 4-phenyl-2H-benzo[b]pyran dissolved in 246 ml of dimethylformamide are added to this solution. The solution is stirred for 48 hours at room temperature. The reaction medium is then poured into an ice-water mixture, neutralized with a concentrated sodium hydroxide solution having a pH greater than 10 and stirred for 1 hour at room temperature. The medium is then extracted three times with diethyl ether.

The organic solution is then washed with water and dried over sodium sulfate. After evaporation, an oil is obtained which is dispersed in 200 ml of heptane. This solution is allowed to stand for 1 hour at −20° C. and then the solid formed is filtered and it is dried. 144.5 g of the expected product are obtained, that is to say a yield of 75.1%. This compound has a melting point of between 78 and 80° C.

TLC: (MERCK "Kieselgel 60" silica gel; $CH_2Cl_2$-hexane: 1–1); Rf=0.5; NMR: ($CDCl_3$): 5.15 (s, 2H); 6.9–7.5 (m, 9H); 9.45 (s, 1H); I.R.: υ CO=1660 $cm^{-1}$.

Step 2

(4-Phenyl-2H-3-benzo[b]pyranyl)methanol.

302.6 g (1.28 mol) of the compound obtained in the preceding step in solution in a mixture of 7.7 litres of methanol and 260 ml of water are placed in a 20-litre reactor kept under a nitrogen atmosphere. 53.3 g (1.4088 mol) of sodium borohydride are added in small portions to this solution kept at room temperature. At the end of the addition, the reaction medium is stirred for 30 minutes. After evaporation of the solvent, the residue is dissolved in diethyl ether and the organic solution is washed with water until a pH of the washings equal to 7 is obtained. After evaporation of the solvent, an oil is obtained which is crystallized from 200 ml of pentane. After 2 hours at −20° C., the solid obtained is drained. 269.3 g of the expected product are thus obtained, that is to say a yield of 88.3%. The melting point of this compound is between 67 and 68° C.

TLC: (MERCK "Kieselgel 60" silica gel; AcOEt-hexane: 1–1); Rf=0.5; I.R.: υ CO=3356 $cm^{-1}$.

Step 3

3-(Chloromethyl)-4-phenyl-2H-benzo[b]pyran.

269.3 g (1.13 mol) of the compound obtained in the preceding step in solution in 2.7 litres of toluene are placed in a 6-litre reactor kept under a nitrogen atmosphere and protected from moisture.

165 ml (2.16 mol) of thionyl chloride are added dropwise to this solution kept at room temperature. The reaction medium gradually becomes dark red. At the end of the addition, the reaction medium is stirred for minutes. After evaporation of the solvent, the residue is dissolved in diethyl ether. The organic solution is washed with water until a pH of the washings equal to 7 is obtained, and then dried over sodium sulfate. After evaporation of the solvent, 291.2 g of an oil are obtained, that is to say a yield of about 100%.

Step 4

2-(4-Phenyl-2H-3-benzo[b]pyranyl)acetonitrile.

58.2 g (1.186 mol) of sodium cyanide in suspension in 1.36 litres of dimethyl sulfoxide are placed in a 6-litre reactor kept under a nitrogen atmosphere and protected from moisture. 291.2 g (1.13 mol) of the compound obtained in the preceding step in solution in 1.2 litres of dimethyl sulfoxide are added dropwise to this solution kept at room temperature. At the end of the addition, the reaction medium is stirred for 48 hours. The solution is poured into an ice-water mixture. The precipitate formed is extracted three times with methylene chloride. The organic solution is washed with water and then dried over sodium sulfate. After evaporation of the solvent, 262 g of an oil are obtained. This oil is dissolved in a methylene chloride-heptane: 1–1 mixture and is chromatographed on a silica gel. After evaporation of the solvent, 196.7 g of an oil are obtained, that is to say a yield of 70.5%.

TLC: (MERCK "Kieselgel 60" silica gel; AcOEt-hexane: 1–3); Rf=0.63; I.R.: υ CN=2247 $cm^{-1}$; NMR: ($CDCl_3$): 3.1 (s, 2H); 5.0 (s, 2H); 6.65 (dd, 1H); 6.8 (dd, 1H); 6.9 (dd, 1H); 7.15–7.3 (m, 3H); 7.4–7.6 (m, 3H).

Step 5

2-(4-Phenyl-2H-3-benzo[b]pyranyl)acetic acid.

56.7 g (0.229 mol) of the compound obtained in the preceding step in solution in a mixture of 300 ml of acetic acid and 300 ml of a concentrated hydrochloric acid solution are heated under reflux for 3 hours in a 2-litre reactor. After cooling (standing for 12 hours at room temperature), a precipitate forms. After draining and rinsing with water, the precipitate is solubilized in methylene chloride. The organic phase is washed with water (until a pH of the washings equal to 7 is obtained), dried over sodium sulfate and evaporated off. The solid obtained is dispersed in pentane and then drained. 54 g of the expected product are thus obtained, that is to say a yield of 88%. This compound has a melting point of between 147 and 149° C.

I.R.: υ CO=1721 $cm^{-1}$; NMR: ($CDCl_3$): 3.1 (s, 2H); 4.8 (s, 2H); 6.6–7.3 (m, 10H).

2—Other compounds of formula II in which Z is —$CHR_9$—.

By applying the operating protocol described above for the preparation of 2-(4-phenyl-2H-3-benzo[b]-pyranyl) acetic acid, the compounds assembled in Table 3 below are prepared.

TABLE 3

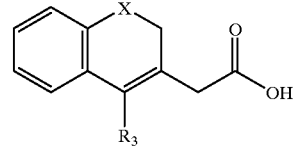

| Preparation No. | X | $R_3$ | Melting point (° C.) |
|---|---|---|---|
| III.2.1 | O | 4-F—$C_6H_4$— | oil |
| III.2.2 | $CH_2$ | $C_6H_5$— | oil |

These compounds were obtained via the intermediates of Tables 4 to 7 below.

TABLE 4

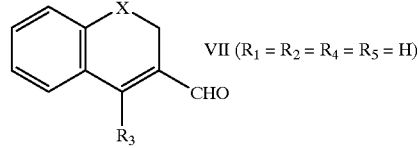

VII ($R_1 = R_2 = R_4 = R_5 = H$)

| Intermediate No. | X | $R_3$ | Melting point (° C.) |
|---|---|---|---|
| VII.1 | O | 4-F—$C_6H_4$— | 113–115 |
| VII.2 | $CH_2$ | $C_6H_5$— | oil |

More precisely, these compounds are prepared by carrying out the procedure as in step 1 of § III.1 above from the appropriate reagents.

TABLE 5

VI ($R_1 = R_2 = R_4 = R_5 = H$)

| Intermediate No. | X | $R_3$ | Melting point (° C.) |
|---|---|---|---|
| VI.1 | O | 4-F—$C_6H_4$— | 96–98 |
| VI.2 | $CH_2$ | $C_6H_5$— | oil |

More precisely, these compounds were prepared by carrying out the procedure as in step 2 of § III.1 above from the appropriate reagents.

TABLE 6

V ($R_1 = R_2 = R_4 = R_5 = H$)

| Intermediate No. | X | $R_3$ | Melting point (° C.) |
|---|---|---|---|
| V.1 | O | 4-F—$C_6H_4$— | oil |
| V.2 | $CH_2$ | $C_6H_5$— | oil |

More precisely, these compounds were prepared by carrying out the procedure as in step 3 of § III.1 above from the appropriate reagents.

TABLE 7

IV ($R_1 = R_2 = R_4 = R_5 = H$)

| Intermediate No. | X | $R_3$ | Melting point (° C.) |
|---|---|---|---|
| IV.1 | O | 4-F—$C_6H_4$— | oil |
| IV.2 | $CH_2$ | $C_6H_5$— | oil |

More precisely, these compounds were prepared by carrying out the procedure as in step 4 of § III.1 above from the appropriate reagents.

EXAMPLE 1

N-[2,4-Dimethylthio-6-methyl-3-pyridyl]-2-(4-phenyl-2H-3-benzo[b]pyranyl)acetamide.

45 g (0.169 mol) of 2-(4-phenyl-2H-3-benzo[b]pyranyl) acetic acid and 23.5 ml (0.169 mol) of triethylamine in solution in 338 ml of methylene chloride are placed in a 2-litre reactor protected from moisture. 43.02 g (0.169 mol) of bis(2-oxo-3-oxazolidinyl)phosphinic acid chloride are added in small portions to this solution kept between 0 and 5° C., following which the reaction mixture is stirred for 1 h. 33.84 g (0.169 mol) of 2,4-dimethylthio-6-methyl-3-pyridylamine are then added all at once. 23.5 ml (0.169 mol) of triethylamine in solution in 68 ml of methylene chloride are then poured dropwise into this solution kept between 0 and 5° C., over a period of one hour. The reaction medium is gradually solubilized and is stirred for 12 hours at room temperature. After the addition of water and methylene chloride, a precipitate is filtered and discarded. The reaction medium is allowed to separate out by settling and then the organic phase is washed with water and then with a hydrochloric acid solution and finally with water until a pH of the washings equal to 7 is obtained. After drying over sodium sulfate, the organic phase is evaporated off. The solid obtained is dispersed for 30 minutes in 300 ml of ethanol and then drained. 52 g of the expected product are obtained (in a wet state). The product is then recrystallized from 4.5 litres of ethanol and placed for 12 hours at −20° C. After draining, the solid obtained is dried in a ventilated oven (2 hours 30 minutes at 50–55° C.) and then for 20 hours at 95° C. 30.5 g of the expected compound are thus obtained, that is to say a yield of 40.2%. This compound has a melting point of between 201–203° C.

TLC: (MERCK "Kieselgel 60" silica gel; AcOEt-hexane: 1–1); Rf=0.51; I.R.: υ NH=3198 cm$^{-1}$; CO=1661 cm$^{-1}$; NMR: (CDCl$_3$): 2.3 (sd, 3H); 2.4 (s, 3H); 2.8–3.1 (sd, 2H); 4.8–5.0 (sd, 2H); 6.2–7.4 (m, 11H). Percentage analysis: $C_{25}H_{24}N_2O_2S_2$ MW=448.5.

|  | C | H | N | S |
|---|---|---|---|---|
| Calculated % | 66.94 | 5.39 | 6.25 | 14.29 |
| Found % | 66.65 | 5.34 | 6.23 | 14.07 |

EXAMPLE 2

N-[2,4-Dimethylthio-6-methyl-3-pyridyl]-3-(4-phenyl-2H-3-benzo[b]pyranyl)prop-2-enamide 1 g (3.59 mmol) of 3-(4-phenyl-2H-3-benzo[b]-pyranyl) prop-2-enoic acid in solution in 30 ml of methylene chloride is placed in a 250-ml reactor protected from moisture, and a drop of dimethyl-formamide is added thereto. 0.39 ml (3.76 mmol) of oxalyl chloride is poured dropwise into this solution kept at room temperature. The reaction medium is then heated under reflux for 1 hour. After evaporation of the solvent, the reaction medium is taken up in 20 ml of methylene chloride. This solution is then poured into a mixture kept between 0 and 5° C. consisting of 0.75 g (3.76 mmol) of 2,4-dimethylthio-6-methyl-3-pyridylamine, 2.2 ml of pyridine and 30 ml of methylene chloride. The resulting reaction medium is stirred at room temperature for 12 hours. After addition of water, the organic phase is separated after settling out, washed with a 2 normal hydrochloric acid solution and then with water until a pH of the washings equal to 7 is obtained. After drying over sodium sulfate, the organic phase is evaporated off. The resulting solid is dispersed in 10 ml of hexane and drained. 1.1 g of the expected compound are thus obtained in the crude state. The latter is recrystallized from 140 ml of ethanol (12 hours at −20° C.) and then drained and dried. 0.77 g of the expected compound is obtained, that is to say a yield of 46.7%. This compound has a melting point of between 225 and 227° C.

|  | C | H | N | S |
|---|---|---|---|---|
| Calculated % | 67.80 | 5.25 | 6.08 | 13.92 |
| Found % | 67.54 | 5.25 | 6.15 | 14.15 |

TLC: (MERCK "Kieselgel 60" silica gel; AcOEt-hexane: 1–1); Rf=0.59; I.R.: υ NH=3253, CO=1652; NMR: (CDCl$_3$): 2.35 (s, 3H); 2.4 (s, 3H); 2.45 (s, 3H); 4.7 (s, 1H); 5.0 (s, 1H); 5.9–5.95 (d, 1H); 6.25 (s, 1H); 6.58 (d, 1H); 6.62–6.80 (m, 2H); 6.84–6.87 (d, 1H); 7.05–7.17 (m, 3H); 7.3–7.4 (m, 4H). Percentage analysis: C$_{26}$H$_{24}$N$_2$O$_2$S$_2$ MW 460.62.

The compounds of Examples 3 to 5 below were prepared according to the procedure set out in Example 1, from appropriate reagents.

The compounds of Examples 6 to 15 below, for their part, were prepared on the model of the procedure of Example 2 from appropriate reagents.

These compounds are assembled in Tables 8 and 9 below.

TABLE 8

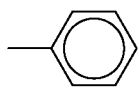

| Ex. | X | R$_1$ | R$_2$ | R$_3$ | R$_6$ + R$_7$ | R$_9$ | Ar | Melting point (° C.) |
|---|---|---|---|---|---|---|---|---|
| 3 | O | H | H | 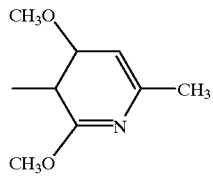 | Bond | H | 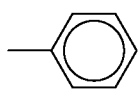 | 184–186 |
| 4 | CH$_2$ | H | H | 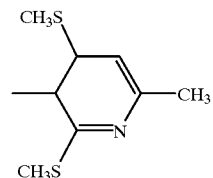 | Bond | H | 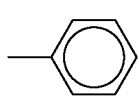 | 218–220 |
| 5 | O | H | H | 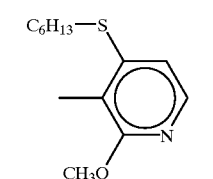 | Bond | H | 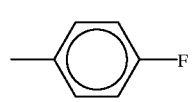 | 127–130 |
| 6 | O | H | H | 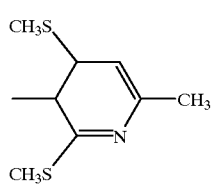 | Bond | H | (structure) | 234–236 |

TABLE 8-continued
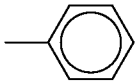
| Ex. | X | $R_1$ | $R_2$ | $R_3$ | $R_6 + R_7$ | $R_9$ | Ar | Melting point (° C.) |
|---|---|---|---|---|---|---|---|---|
| 7 | O | H | H | tolyl | Bond | —$C_4H_9$ | 4-CH3S, 3-CH3, 6-CH3, 2-CH3S pyridine | 117–119 |
| 8 | O | H | H | tolyl | Bond | H | 2,6-diiPr phenyl | 250–253 |
TABLE 9
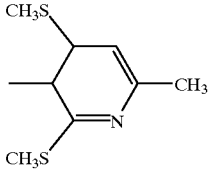
| Ex. | X | $R_1$ | $R_2$ | $R_3$ | $R_6 + R_7$ or R6, R7 | $R_{10} + R_{11}$ or R10, R11 | Ar | Melting point (° C.) |
|---|---|---|---|---|---|---|---|---|
| 9 | S | H | H | tolyl | bond | bond | 4-CH3S, 3-CH3, 6-CH3, 2-CH3S pyridine | 215–217 |
| 10 | O | —$(CH_2)_4$— | | 4-F phenyl | bond | bond | 4-CH3S, 3-CH3, 6-CH3, 2-CH3S pyridine | 215–217 |
| 11 | O | —$(CH_2)_4$— | | 4-F phenyl | bond | H, H | 4-CH3S, 3-CH3, 6-CH3, 2-CH3S pyridine | 214–217 |

TABLE 9-continued

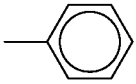

| Ex. | X | $R_1$ | $R_2$ | $R_3$ | $R_6 + R_7$ or R6, R7 | $R_{10} + R_{11}$ or R10, R11 | Ar | Melting point (° C.) |
|---|---|---|---|---|---|---|---|---|
| 12 | S | H | H | 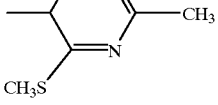 | bond | H, H |  | 170–172 |
| 13 | O | H | H | 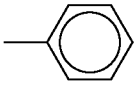 | H, H | H, H | 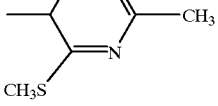 | 166–168 |
| 14 | S | H | H |  | bond | Bond | 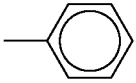 | 248–250 |
| 15 | S | H | H | 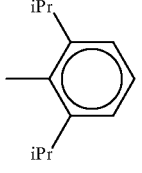 | bond | H, H |  | 194–196 |

In these two tables, "bond" means that $R_6$ and $R_7$, respectively $R_{10}$ and $R_{11}$, together form a bond.

EXAMPLE 16

2-(4-Phenyl-2H-3-benzo[b]pyranyl)hexanoic acid 3.1 ml (22 mmol) of diisopropylamine in solution in 20 ml of tetrahydrofuran are placed in a 250-ml reactor protected from moisture, and then 13.75 ml (22 mmol) of n-butyllithium in hexane (1.6 M) are added dropwise to this solution kept at 0° C. After stirring the reaction medium for 15 minutes at 0° C., 2.66 g (10 mmol) of 2-(4-phenyl-2H-3-benzo[b]-pyranyl)acetic acid are added dropwise to this solution kept at 0° C. The reaction medium is stirred for 2 hours at 0° C. and then 1.18 ml (11 mmol) of 1-bromobutane are poured into this solution kept at this temperature of 0° C. The reaction mixture is stirred for 72 hours at room temperature. After addition of water and hydrochloric acid (2 M), the reaction mixture is extracted with diethyl ether. The organic phase, after washing with water, is dried and then evaporated off. The oil obtained is chromatographed on a silica gel (eluent: methylene chloride). After evaporation of the solvent, the crystals obtained are dispersed in pentane and then drained. 1.7 g of the expected compound are thus obtained, that is to say a yield of 52.8%. This compound has a melting point of between 117 and 119° C.

TLC (MERCK "Kieselgel 60" silica gel; AcOEt-hexane: 1–1); Rf=0.5; I.R.: υ CO=1697.

EXAMPLE 17

N-[2,4-Dimethylthio-6-methyl-3-pyridyl]-4-(4-phenyl-2H-3-benzo[b]pyranyl)but-3-enamide Step 1

4-(4-Phenyl-2H-3-benzo[b]pyranyl)but-2-en-1-oic acid 1.9 g (0.008 mol) of 4-phenyl-2H-3-benzo[b] pyranylcarboxaldehyde and 3.5 g (0.0084 mol) of 1-carboxypropylphosphonium bromide in suspension in 20 ml of tetrahydrofuran are placed in a reactor kept protected from moisture. A solution of 1.9 g (0.0176 mol) of potassium tert-butoxide in 10 ml of tetrahydrofuran is added to this suspension over 1 hour at 0° C. The reaction medium is stirred for 30 minutes between 0 and 5° C. and then for 1 hour at room temperature. The reaction medium is then poured into an ice-water mixture and then extracted with diethyl ether.

The aqueous phase is acidified with concentrated hydrochloric acid (pH=2). After extraction of the aqueous phase with ethyl acetate, the organic phase is dried over sodium sulfate and evaporated. 2 g of a solid are obtained, which solid is dissolved in a methylene chloride-ethyl acetate: 9-1 mixture and is chromatographed on a silica gel. After evaporation of the solvent, 0.7 g of solid is obtained, that is to say a yield of 29.9%.

TLC: (MERCK "Kieselgel 60" silica gel; AcOEt-CH$_2$Cl$_2$—MeOH: 45-45-10); Rf=0.65; I.R. $\gamma$CO$_2$H=1718 cm$^{-1}$.

Step 2

N-[2,4-Dimethylthio-6-methyl-3-pyridyl]-4-(4-phenyl-2H-3-benzo[b]pyranyl)but-3-enamide is prepared under the conditions of Example 1 from 4-(4-phenyl-2H-3-benzo[b]pyranyl)but-3-en-1-oic acid and 2,4-dimethylthio-6-methyl-3-pyridylamine.

Melting point=204–206° C. TLC: (MERCK "Kieselgel 60" silica gel; AcOEt-hexane: 1-1; Rf=0.6); I.R.: $\gamma$NH=3203 cm$^{-1}$; $\gamma$CO=1651 cm$^{-1}$; NMR: (CDCl$_3$): 2.4 (s, 3H); 2.55 (s, 6H); 2.9–3.2 (m, 2H); 5.05–5.15 (m, 2H); 5.9 (m, 1H); 6.3 (d, 1H); 6.6–7.5 (m, 11H).

What is claimed is:

1. A compound of formula I

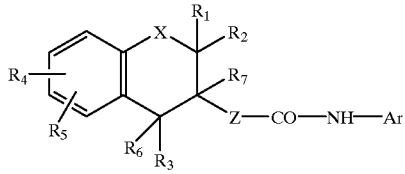

(I)

in which X is O or S;

R$_1$ and R$_2$, which may be identical or different, are hydrogen, (C$_1$–C$_6$)alkyl or (C$_3$–C$_8$)cycloalkyl, or alternatively R$_1$ and R$_2$, together with the carbon atom bearing them, form (C$_3$–C$_8$)cycloalkyl;

R$_3$ is a (C$_6$–C$_{12}$)aryl optionally substituted with one or more Y radicals, which may be identical or different;

Y is halogen, a (C$_1$–C$_6$)alkyl optionally substituted with one or more halogens, a (C$_1$–C$_6$)alkoxy optionally substituted with one or more halogens, a (C$_1$–C$_6$)alkylthio optionally substituted with one or more halogens, (C$_1$–C$_7$)acylamino, (C$_1$–C$_3$)acyloxy, hydroxyl, nitro, cyano, amino, (C$_1$–C$_6$)alkylamino, di-(C$_1$–C$_6$)alkylamino, pyrrolidono, piperidino, morpholino, (C$_1$–C$_4$)alkylsulfonylamino, (C$_2$–C$_5$)alkoxycarbonyl, carboxyl, (C$_2$–C$_6$)alkylcarbonyl, carbamoyl, (C$_2$–C$_5$)alkylcarbamoyl, di-(C$_2$–C$_5$)alkylcarbamoyl or (C$_1$–C$_6$)alkyl-sulfonyl;

R$_4$ and R$_5$, which may be identical or different, are a Y radical or alternatively a hydrogen atom;

Ar is one of the following groups B or C:

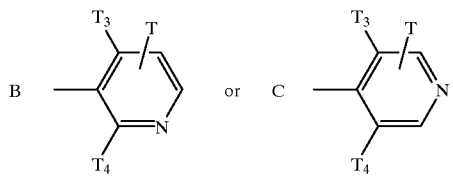

T$_1$ and T$_2$, which may be identical or different, are halogen, (C$_1$–C$_6$)alkoxy, (C$_1$–C$_6$)alkylthio or (C$_1$–C$_6$)alkyl;

T is a hydrogen atom or (C$_1$–C$_6$)alkyl;

T$_3$ and T$_4$, which may be identical or different, are (C$_1$–C$_6$)alkyl, (C$_1$–C$_6$)alkoxy, (C$_1$–C$_6$)alkylthio, (C$_6$–C$_{12}$)arylthio, (C$_1$–C$_6$)alkoxycarbonyl, (C$_1$–C$_6$)alkylcarbonyl, (C$_6$–C$_{12}$)arylcarbonyl or —(CH$_2$)$_p$—OR in which p is 1, 2, 3 or 4 and R is (C$_2$–C$_3$)alkyl, R$_6$ and R$_7$ are each a hydrogen atom or alternatively R$_6$ and R$_7$ together are a bond;

Z is either (i) the divalent group —CHR$_9$— in which R$_9$ is a hydrogen atom or (C$_1$–C$_6$)alkyl;

or (ii) the divalent group —CHR$_{10}$—CHR$_{11}$— in which R$_{10}$ and R$_{11}$ together form a bond such that Z is —CH=CH— or alternatively R$_{10}$ and R$_{11}$, which may be identical or different, are as defined above for R$_9$;

or (iii) the divalent group —CHR$_{12}$—CHR$_{13}$—CH$_2$— in which R$_{12}$ and R$_{13}$ together form a bond such that Z is —CH=CH—CH$_2$—, or alternatively R$_{12}$ and R$_{13}$, which may be identical or different, are as defined above for R$_9$, as well as its addition salts with a pharmaceutically acceptable acid or base.

2. A compound according to claim 1, wherein Y is halogen, (C$_1$–C$_6$)alkyl, (C$_1$–C$_6$)alkoxy or trifluoromethyl.

3. A compound according to claim 1, wherein:

R$_1$ and R$_2$, which may be identical or different, are hydrogen or alternatively R$_1$ and R$_2$, together with the carbon atom bearing them, form (C$_3$–C$_8$)cycloalkyl;

R$_3$ is a (C$_6$–C$_{12}$)aryl optionally substituted with one or more Y radicals, which may be identical or different;

Y is halogen;

R$_4$ and R$_5$ are each a hydrogen atom;

Ar is one of the following groups B or C:

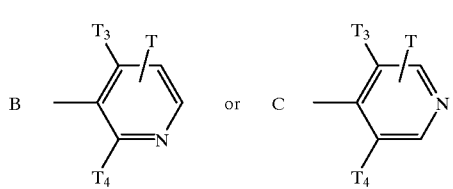

T$_1$ and T$_2$, which may be identical or different, are (C$_1$–C$_6$)alkyl;

T is a hydrogen atom or (C$_1$–C$_6$)alkyl;

T$_3$ and T$_4$, which may be identical or different, are (C$_1$–C$_6$)alkyl, (C$_1$–C$_6$)alkoxy or (C$_1$–C$_6$)alkylthio;

R$_6$ and R$_7$ are each a hydrogen atom or alternatively R$_6$ and R$_7$ together are a bond;

Z is either (i) the divalent group —CHR$_9$— in which R$_9$ is a hydrogen atom or (C$_1$–C$_6$)alkyl; or (ii) the divalent group —CHR$_{10}$—CHR$_{11}$— in which R$_{10}$ and R$_{11}$ together form a bond such that Z is —CH=CH—, or alternatively R$_{10}$ and R$_{11}$ are each a hydrogen atom.

4. A compound according to claim 1, wherein R$_1$ and R$_2$ are a hydrogen atom.

5. A compound according to claim 1 wherein Z is —CHR$_{12}$—CHR$_{13}$—CH$_2$.

6. A compound according to claim 1, wherein X is O or S and R$_1$ and R$_2$, together with the carbon atom bearing them, form a (C$_3$–C$_8$)cycloalkyl.

7. A compound according to claim 1 wherein X is O or S and Z is chosen from:
   (i) —CH=CH—, and
   (ii) —CH=CH—CH$_2$—.

8. A compound according to claim 1, wherein Ar is chosen from 2,4-dimethylthio-6-methyl-3-pyridyl; and 2-methoxy-4-hexylthio-3-pyridyl.

9. A method of preparing a compound of formula I according to claim 1, which comprises coupling an acid of formula II, in activated form,

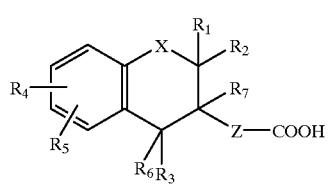

in which R$_1$, R$_2$, R$_3$, R$_4$, R$_5$, R$_6$, R$_7$ and Z are as defined in claim 1, with an aromatic amine of formula III:

Ar—NH$_2$ (III)

in which Ar is as defined in claim 1.

10. A method according to claim 9, wherein the coupling of the compound of formula II and of the amine III comprises:
   (i) activating the acid of formula II by formation of an acid chloride, of an ester or of a mixed anhydride thereof; and
   (ii) reacting the amine of formula III with the compound resulting from step (i).

11. A method according to claim 9, which comprises:
   (i) treating an acid of formula II with bis(2-oxo-3-oxazolidinyl)phosphinic acid in the presence of a base; and then
   (ii) reacting an amine of formula III with the compound obtained in step (i).

12. A method according to claim 9, which comprises:
   (i) treating an acid of formula II with oxalyl chloride in the presence of dimethylformamide; and then
   (ii) reacting an amine of formula III with the compound obtained in step (i).

13. A pharmaceutical composition comprising at least one compound according to claim 1, as active ingredient in combination with one or more pharmaceutically acceptable vehicles.

14. A pharmaceutical composition of claim 13 which exhibits a hypolipidemic or anti-atherosclerotic activity, is in the form of an assay unit, and contains 10 mg to 500 mg of active ingredient mixed with a pharmaceutically acceptable excipient.

15. A method comprising administering to a patient a compound according to claim 1 for the treatment of hyperlipidemia.

16. A method comprising administering to a patient a compound according to claim 1 for the treatment of atherosclerosis.

17. A compound of formula I according to claim 1

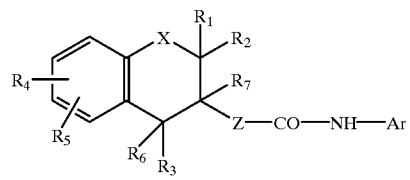

in which X is O,

R$_1$ and R$_2$, which may be identical or different, are hydrogen, (C$_1$–C$_6$)alkyl or (C$_3$–C$_8$)cycloalkyl, or alternatively R$_1$ and R$_2$, together with the carbon atom bearing them, form (C$_3$–C$_8$)cycloalkyl;

R$_3$ is a (C$_6$–C$_2$)aryl optionally substituted with one or more Y radicals, which may be identical or different;

Y is halogen, a (C$_1$–C$_6$)alkyl optionally substituted with one or more halogens, a (C$_1$–C$_6$)alkoxy optionally substituted with one or more halogens, a (C$_1$–C$_6$) alkylthio optionally substituted with one or more halogenis, (C$_1$–C$_7$)acylamino, (C$_1$–C$_3$)acyloxy, hydroxyl, nitro, cyano, amino, (C$_1$–C$_6$)alkylamino, di-(C$_1$–C$_6$)alkylamino, pyrrolidono, peperidino maperidino, morpholino, (C$_1$–C$_4$)alkylsulfonylamino, (C$_2$–C$_5$)alkoxycarbonyl, carboxyl, (C$_2$–C$_6$) alkylcarbonyl, carbamoyl, (C$_2$–C$_5$)alkylcarbamoyl, di-(C$_2$–C$_5$)alkylcarbamoyl or (C$_1$–C$_6$))alkylsufonyl;

R$_4$ and R$_5$, which may be identical or different, are a Y radical or alternatively a hydrogen atom;

Ar is:

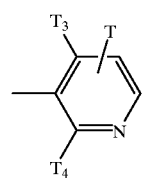

T is a hydrogen atom or (C$_1$–C$_6$)alkyl;

T$_3$ and T$_4$, which may be identical or different, are (C$_1$–C$_6$)alkylthio;

R$_6$ and R$_7$ are each a hydrogen atom or alternatively

R$_6$ an d R$_7$ together are a bond;

Z is either
   (i) the divalent group —CHR$_9$— in which R$_9$ is a hydrogen atom or (C$_1$–C$_6$)alkyl;
   or (ii) the divalent group —CHR$_{10}$—CHR$_{11}$— in which R$_{10}$ and R$_{11}$ together form a bond such that Z is —CH=CH— or alternatively R$_{10}$ and R$_{11}$, which may be identical or different, are as defined above for R$_9$;

or (iii) the divalent group —$CHR_{12}$—$CHR_{13}$—$CH_2$— in which $R_{12}$ and $R_{13}$ together form a bond such that Z is —CH=CH—$CH_2$—, or alternatively $R_{12}$ and $R_{13}$, which may be identical or different, are as defined above for $R_9$, as well as its addition salts with a pharmaceutically acceptable acid or base.

* * * * *

UNITED STATES PATENT AND TRADEMARK OFFICE
CERTIFICATE OF CORRECTION

PATENT NO. : 6,339,097 B1
DATED : January 15, 2002
INVENTOR(S) : Diedier Festal et al.

It is certified that error appears in the above-identified patent and that said Letters Patent is hereby corrected as shown below:

Column 30,
Line 33, delete "halogenis" and insert -- halogens --;
Line 35, delete "poperidino" and insert -- piperidino --;
Line 36, delete "maperidino".

Signed and Sealed this

Eleventh Day of June, 2002

*Attest:*

JAMES E. ROGAN
*Attesting Officer*     *Director of the United States Patent and Trademark Office*